US012751840B2

(12) United States Patent
Seifert

(10) Patent No.: US 12,751,840 B2
(45) Date of Patent: Oct. 6, 2026

(54) METHOD FOR CONFIGURING A CONTROLLER AND ORTHOPEDIC DEVICE, AND COMPUTER PROGRAM PRODUCT

(71) Applicant: Otto Bock Healthcare Products GmbH, Vienna (AT)

(72) Inventor: Dirk Seifert, Vienna (AT)

(73) Assignee: Otto Bock Healthcare Products GmbH, Vienna (AT)

( * ) Notice: Subject to any disclaimer, the term of this patent is extended or adjusted under 35 U.S.C. 154(b) by 862 days.

(21) Appl. No.: 18/246,813

(22) PCT Filed: Sep. 22, 2021

(86) PCT No.: PCT/EP2021/076071
§ 371 (c)(1),
(2) Date: Mar. 27, 2023

(87) PCT Pub. No.: WO2022/063834
PCT Pub. Date: Mar. 31, 2022

(65) Prior Publication Data

US 2023/0363930 A1 Nov. 16, 2023

(30) Foreign Application Priority Data

Sep. 28, 2020 (DE) ........................ 102020125255.2

(51) Int. Cl.
*A61F 2/70* (2006.01)
*G06F 3/04847* (2022.01)
*G06F 3/0487* (2013.01)

(52) U.S. Cl.
CPC ............ *A61F 2/70* (2013.01); *G06F 3/04847* (2013.01); *G06F 3/0487* (2013.01); *A61F 2002/704* (2013.01)

(58) Field of Classification Search
CPC ...... A61F 2/70; A61F 2/72; A61F 2/76; A61F 2/54; A61F 2/583; A61F 2002/704;
(Continued)

(56) References Cited

U.S. PATENT DOCUMENTS

2014/0172120 A1* 6/2014 Steele ........................ A61F 2/64
623/39
2015/0035194 A1 2/2015 Dong et al.
2020/0326958 A1* 10/2020 Blumenthal .............. G06F 8/65

FOREIGN PATENT DOCUMENTS

DE 102017119490 B3 11/2018
DE 102017131190 A1 6/2019
(Continued)

OTHER PUBLICATIONS

International Search Report and Written Opinion for International Patent Application No. PCT/EP2021/076071, mailed Jan. 4, 2022.

*Primary Examiner* — Nhi Q Bui
(74) *Attorney, Agent, or Firm* — Goodwin Procter LLP

(57) ABSTRACT

The invention relates to a method for configuring a controller of an orthopedic device, which has at least one data processing device (10), sensors (20) coupled thereto and an actuator (30) which is activated and/or deactivated by the data processing device (10), the controller having a basic function block (40), in which a basic functionality of the actuator (30) is defined, a plurality of additional function blocks (60), which have different additional functionalities, being provided to an interface device (50) from a memory (15) and at least one additional function block (60) being selected and added to the basic function block (40) by way of the interface device (50), there being an interface (46) between the basic function block (40) and the at least one additional function block (60), the compatibility of the functionalities being checked and an overall functionality being generated at said interface, an adjustment of at least
(Continued)

Figure 1:
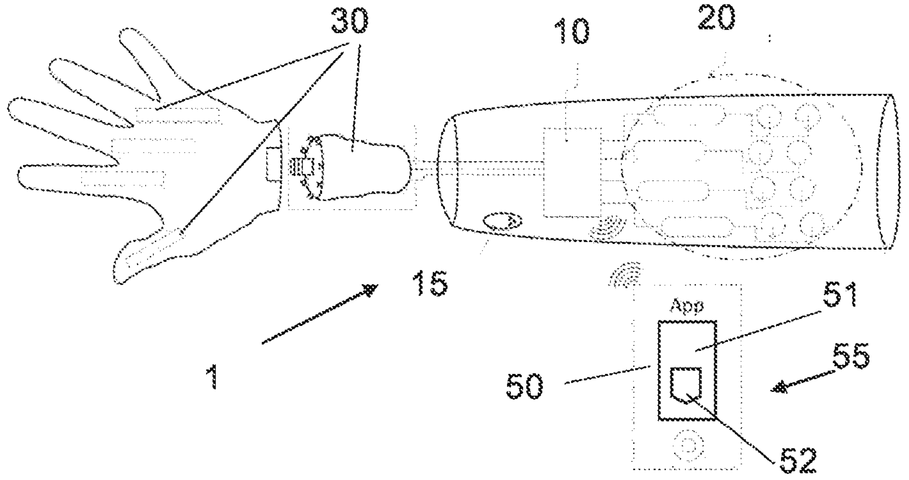

one functionality being carried out to establish compatibility, or an inclusion of the additional functionality being rejected, in the case of lack of compatibility at the outset.

15 Claims, 7 Drawing Sheets

(58) Field of Classification Search
CPC .......... A61F 2002/543; A61F 2002/707; A61F 2002/7615; A61F 2002/7695; G06F 3/04847; G06F 3/0487
See application file for complete search history.

(56) References Cited

FOREIGN PATENT DOCUMENTS

| | | |
|---|---|---|
| DE | 102017131194 A1 | 6/2019 |
| DE | 102017131195 A1 | 6/2019 |

* cited by examiner

METHOD FOR CONFIGURING A CONTROLLER AND ORTHOPEDIC DEVICE, AND COMPUTER PROGRAM PRODUCT

CROSS-REFERENCE TO RELATED APPLICATIONS

This application is a U.S. national phase filing claiming the benefit of and priority to International Patent Application No. PCT/EP2021/076071, filed Sep. 22, 2021, which claims priority from and the benefit of German Patent Application No. 10 2020 125 255.2, filed Sep. 28, 2020. The entire contents of these applications are incorporated herein by reference.

The invention relates to a method for configuring a control for an orthopedic device having at least one data processing device, sensors coupled thereto, and an actuator which is activated and/or deactivated by the data processing device, the control having a basic function block in which a basic functionality of the actuator is defined. The invention likewise relates to an orthopedic device comprising a data processing device which is configured and designed to carry out the method, and to a computer program product comprising a program code.

Prostheses serve to replace missing or no longer existing limbs. In addition to an approximation of the external shape, prostheses should also replicate the function of the limb to be replaced as completely as possible. In addition to purely mechanical prostheses, there are a multiplicity of prostheses that are electronically controlled. By way of example, the control relates to the adaptation of prosthetic devices to different usage conditions or usage requirements. Prostheses often have more than one component and these components can be adjusted or displaced relative to one another. By way of example, prosthetic joints are provided for pivoting an upper part relative to a lower part, with a resistance device or a drive being arranged between the upper part and the lower part and being able to be altered on the basis of sensor data evaluated in a control device. An actuator, for example a motor or another adjustment device, can adjust valves in order to change resistances to movement.

An electric drive can be switched into a generator mode in order to provide resistance to pivoting, but the drive can alternatively be activated in order to perform or assist movement. A magnetic field can be generated, for example by way of an electromagnet, in order to change viscosity properties of a magnetorheological medium. The electromagnet would then be a corresponding actuator. A corresponding statement applies to other displaceable devices or components in which an actuator can be adjusted.

Orthoses are orthopedic aids that are applied to an existing limb and that guide, limit or support movements. Drives or resistance devices, which can be adjusted or set in a manner corresponding to devices on prostheses, can be arranged between components connected to one another in articulated fashion. Here, too, the adjustment is based on sensor data that are transmitted to a data processing device.

The sensor data and the commands for the adjustment can be transmitted wirelessly to the actuator. Within the scope of this application, orthoses are also understood to mean exoskeletons which are placed on the body of a patient and form an external support structure, in particular to guide and influence the movements of a user, for example to support said movements with drives or to brake said movements using resistance devices. Orthoses and exoskeletons as special cases can also be used and utilized for training purposes or for therapeutic purposes in addition to supporting daily activities.

Current prostheses or orthoses with sensor-based adjustment devices or actuators are supplied with software that is adapted to and configured for the respective patient. Individual parameters can be changed during configuration, for example in order to adapt the damping behavior of a resistance device to the respective user. It is also possible to activate or deactivate individual functions, for example because the patient in question cannot or should not implement this function.

It is also possible to configure what are known as additional modes, which go beyond the basic functionality. By way of example, the additional modes support special activities such as cycling or skiing. The additional modes can be selected by the respective user, and the respective parameters of the additional modes can be adapted. A corresponding selection is also made for orthoses of the lower extremities.

Upper extremity prostheses can likewise be customized. Prosthetic hands have specific gripping modes that can be customized. The adjustments are implemented by the respective orthopedic technician or the operator, and the respective user can switch individually between the individual grip types.

Both the programming and the adjustment by adapting individual parameters are complex. The programming options are usually very limited or not available at all. In addition, there is a risk that an adaptation of an additional mode will have negative effects on already existing functionalities.

The object of the present invention is therefore to provide a method for configuring a control for an orthopedic device, in particular an orthosis or prosthesis or an exoskeleton, with which misprogramming and misconfigurations of the control can be avoided. At the same time, the control should be highly adaptable and the programming should be intuitive and flexible. Simple and safe handling for the respective operator should be guaranteed.

According to the invention, this object is achieved by a method having the features of the main claim and by an orthopedic device and a computer program product having the features of the respective independent claim. Advantageous embodiments and developments of the invention are disclosed in the dependent claims, in the description and in the figures.

The method for configuring a control for an orthopedic device, in particular an orthosis, a prosthesis, or an exoskeleton, having at least one data processing device, sensors coupled thereto, and an actuator which is activated and/or deactivated by the data processing device, the control having a basic function block in which a basic functionality of the actuator is defined, provides for a plurality of add-on function blocks which each have different add-on functionalities to be made available to an interface device from a memory and for at least one add-on function block to be selected via the interface device and added to the basic function block, there being an interface between the basic function block and the at least one add-on function block, at which the compatibility of the respective functionalities of the function blocks is checked and an overall functionality is generated, with, in the case of a lack of compatibility at the outset, at least one functionality being adapted to produce the compatibility or integration of the add-on functionality being rejected. Consequently, a plurality of add-on function blocks which can be combined with the basic function block are available for configuring a control. The basic function block comprises the basic functionalities of the actuator. When controlling a prosthesis or orthosis with an adjustable resistance, this can be the adaptation to the respective movement situation. The orthoses or prostheses can also be arranged on the upper extremities and, in addition to passive resistance devices such as hydraulic dampers, brakes, and magnetorheologically influenceable resistance devices, can alternatively or additionally have active drives such as electric motors or other adjustment devices. When walking on level ground, it is necessary to provide different resistances to flexion or extension in an artificial knee joint. To this end, corresponding resistances are adjusted on the basis of sensor data evaluated in the data processing device in order to achieve a gait behavior that is adapted to walking with a natural knee joint. For example, at the beginning of the stance phase after a heel strike, stance phase flexion can initially be made possible by reducing the flexion resistance. In the further course, the flexion resistance is increased again in order to prevent excessive stance phase flexion. Subsequently, as part of the rollover movement, maintenance of a high flexion resistance is set in order then to allow flexion at the end of the stance phase so that the prosthetic knee joint or orthotic knee joint bends in and allows swinging through when moving forward. This basic functionality for walking on level ground can be supplemented by an add-on function which is stored in a control block as an add-on function block. Such an add-on function can be, for example, walking on a ramp, climbing stairs, or walking at an increased walking speed. What may be true in this context is that the respectively selected add-on function block is not compatible with parts of the basic function block or else is compatible with an already existing add-on function block. Compatibilities may likewise result from already existing combinations of the basic function block with one or more add-on function blocks, with the result that simply adding the add-on function block would result in an overall functionality that is not advantageous or might even be harmful to the user. Therefore, a compatibility check is performed at the interface between the basic function block and the add-on function block or at the interface between the add-on function block and another add-on function block that is already connected to the basic function block. The functionalities of the individual function blocks are checked and the overall functionality of the control is generated therefrom. If the function blocks are not compatible, at least one functionality, in particular the functionality of the newly added add-on function block, can be adapted so that compatibility is achieved. Additionally, functions other than that of the newly added add-on function block can be modified. For example, if the function of the newly added add-on function block is given greater priority or importance than a functionality of an already added add-on function block, the adaptation to be made can be selected via the prioritization. As an alternative to changing one or more functionalities of the basic function block and/or of the one or more add-on function blocks, it is possible that the integration of the add-on functionality of the added add-on function block is rejected because there is a risk or an undesired overall functionality as a result of this add-on functionality or the compensation for the new add-on functionality. This achieves the ability to provide a multiplicity of add-on functionalities in add-on function blocks, which can be combined with one another without further checking, the compatibility being checked automatically and, if necessary, the functions being adapted automatically in order to produce compatibility and overall functionality. If an adaptation cannot be achieved or should not be achieved, the integration of the add-on functionality and hence the combination of an add-on function block with the basic function block or a combination of a basic function block with one or more add-on function blocks can be rejected. Misprogramming as a result of an impermissible combination of functionalities can no longer occur as a result of the method according to the invention.

A development of the invention provides for a plurality of function blocks to be successively added to the add-on function block, with the compatibility with the currently existing overall functionality being checked for each new add-on function block. Hence there is a modular construction starting from the basic function block, with a further addition of a functionality being checked in the order in which further add-on function blocks are added, starting from the overall functionality once the latter has been determined. If, after the addition of two add-on function blocks, an overall functionality is achieved in which some functions originally present in one of the add-on function blocks have been reduced, this already excluded functionality or a restriction in the functional area is no longer taken into account, since it was already excluded or limited in the previous design phase. The effect thereof is that it is no longer necessary to check all combinations of all functionalities for compatibility in order to form an overall functionality. Instead, only the newly added potential of functionalities by way of the new add-on function block is checked for compatibility with the already existing overall functionality.

A development of the invention provides for at least one parameter of the basic functionality and/or add-on functionality to be adjustable via the interface device. Each functionality can consequently be scalable, for example damping settings can be adapted for an adaptation to individual wishes or circumstances. Adaptations can be made, for example, to walking speeds, usage purposes, body weights, levels of activity, or else physiological conditions. In addition to adapting the parameters of the basic functionality, at least one parameter of an add-on functionality can also be created. The degree of adjustability by way of the interface device can be altered depending on the overall functionality achieved. By way of example, adding a further add-on functionality can be followed by a restriction of a parameter range for adjusting a manipulated variable of the basic functionality or else by an exclusion or opening up of a parameter range of the newly added add-on functionality if a specific overall functionality is present.

A prioritization value can be assigned to each add-on functionality, with the compatibility and adaptation of the respective functionality being checked on the basis of the prioritization values. By way of example, if an add-on functionality that is added at a later stage has a higher prioritization than an add-on functionality that was already added previously, then there can be a reorganization and a realignment and recalculation of the overall functionality, which is then aligned on the basis of the respective prioritization values. Thus, a weighting used to construct an overall functionality can be implemented independently of the time or state of the combination of basic function block and a plurality of add-on function blocks. If an add-on function block with the highest priority is only added at a time where three add-on function blocks with lower prioritization values are already present, then the overall functionality is recalculated on the basis of the available prioritization values. If the prioritization values are the same, it is advantageous to use the time of the combination or addition as a benchmark for the order in which the compatibilities are checked and the adaptations to parameter values are made.

A graphical user interface is advantageously provided as the interface device, the add-on functionalities being displayed on said graphical user interface as user interface objects. The representation as graphic blocks can consequently be selected by drag-and-drop from a menu and dragged into a workspace. The function groups or add-on function blocks can then be connected to one another via interfaces, with graphic displays of the respective user interface objects being able to indicate whether combinability is even present.

A development of the invention provides for the compatibility of different add-on function blocks with one another or with the current combination of basic function block and at least one add-on function block to be displayed graphically. By way of example, the graphic display can be implemented by way of geometries or a color coding. A color and/or graphic combinability of an add-on function block with the basic function block and/or another add-on function block can be represented on the user interface objects. The basic combinability can be indicated on the basis of the graphic form of the user interface objects or the color design. By way of example, the same colors can indicate a fundamental combinability. Likewise, a suitability for combinability can be indicated by a similar coloring. By way of example, if the overall functionality is displayed using a red hue, a fundamental combinability can be displayed using a red or orange hue, while a non-combinability can be displayed by way of a blue or a green hue of another add-on function block, for example. Alternatively or additionally, a change in the shape of the user interface objects can indicate whether there is a fundamental combinability. By way of example, if there is a cutout in a contour, combinability is only given with a corresponding bulge or a corresponding projection in a graphical representation of an add-on function block or the representation of the overall functionality. The graphical design or the shape of the user interface objects can change, especially if they have become part of an overall functionality.

The method is advantageously implemented on the data processing device within the orthopedic device. The interface device can also be part of the orthopedic device. Adaptability and usability are made easier if the interface device is designed as a mobile terminal, for example as a cellular phone, tablet, augmented reality device, virtual reality device, mixed reality device, head-mounted display such as HoloLens or Google Glass®, voice interface, or else as a mobile computer which has a wireless connection to the control device or data processing device on the orthopedic device. In principle, the interface device can be a fixed component of the orthopedic device or it can be designed as a separate component and be coupled to the rest of the orthopedic device in a wireless or wired manner.

Not only can an interface to the basic function block be formed on an add-on function block, but an interface for at least one further add-on function block can likewise be formed on an add-on function block, with the result that further add-on function blocks can be fixed to and combined with said add-on function block following its addition.

The basic function block and/or an add-on function block can have a plurality of interfaces, at least one of which is blocked as a result of another interface being occupied with an add-on function block. If a predetermined interface is occupied by an add-on function block that is compatible therewith, an interface available per se may be blocked by this occupancy and no longer be available for further add-on function blocks. This rules out any expansion of the add-on functionality in this area or in the area of the functionality located there.

A development of the invention provides for the compatibility of the function blocks and/or the integration of a plurality of function blocks into an overall functionality to be checked in an external apparatus. By way of example, the external apparatus is part of the interface unit or has a data transmission connection to the interface unit. In particular via a radio connection or via a data transmission network, it is possible to transmit control data and functionalities from the external apparatus to the orthopedic device via the interface unit. The interface unit thus provides a connection between the external apparatus and the orthopedic device, with the interface unit either being arranged securely on the orthopedic device or designed as a separate part coupled to the rest of the orthopedic device. This makes it possible to shift any required significant computing outlay for checking and adapting the respective functionalities to the external apparatus and only still transmit an adaptation service or a change data record to the data processing device of the orthopedic device. A respective adaptation of the overall functionality is then implemented by means of this data record and the actuator is controlled using the respective control signals on the basis of the sensor values or others.

Predefined programs or templates can be used to create a function block; these so-called presets serve as the basis for the creation of individual programs and can be stored in the data processing device, in the interface device or in an external apparatus.

In particular, the data processing device has a communication interface via which data is transmitted to external devices or received from external and/or from external devices. This makes it possible to store an individually created program that was calculated externally or to save a program created in the orthopedic device on an external apparatus, for example on a cellular phone or tablet, or share said created program via a network or cloud. As a result, external maintenance or an external control of a created overall functionality can be implemented. Combinations which were individually created by a user and have different functionalities and set parameters can be checked for appropriateness, adaptability and medical benefit if these data, optionally in connection with movement data from the orthopedic device, are transmitted to an orthopedic technician or another evaluation institution. In particular, there is the option of transferring a configuration of a joint and/or a configuration of function blocks to another joint or another orthopedic device using the external apparatus.

The orthopedic device provides a data processing device which is configured and designed to carry out an above-described method, with a user interface which has input means for receiving user inputs being present. The user interface can be designed and configured as a graphical user interface, but other user interfaces can alternatively be present, for example acoustic user interfaces with voice control or a keyboard.

The computer program with a program code which, when loaded in a data processing device, brings about execution of the method as described above is likewise part of the invention.

Figure 2:
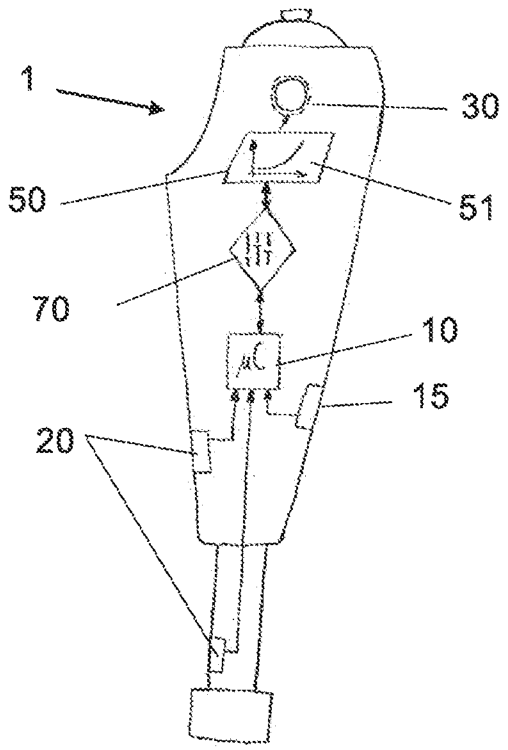
Figure 3:
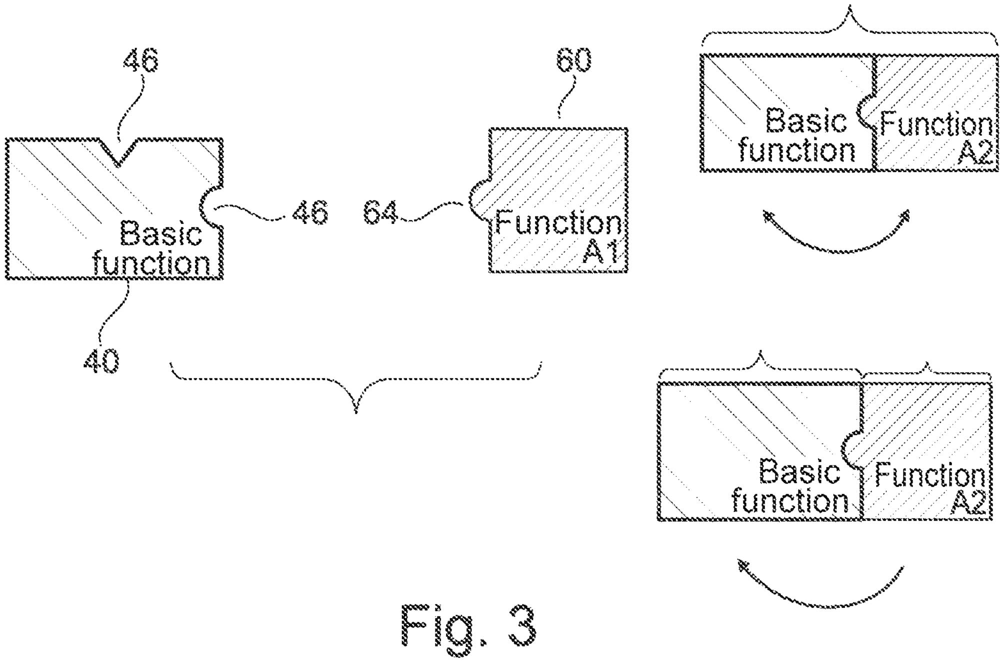
Figure 4:
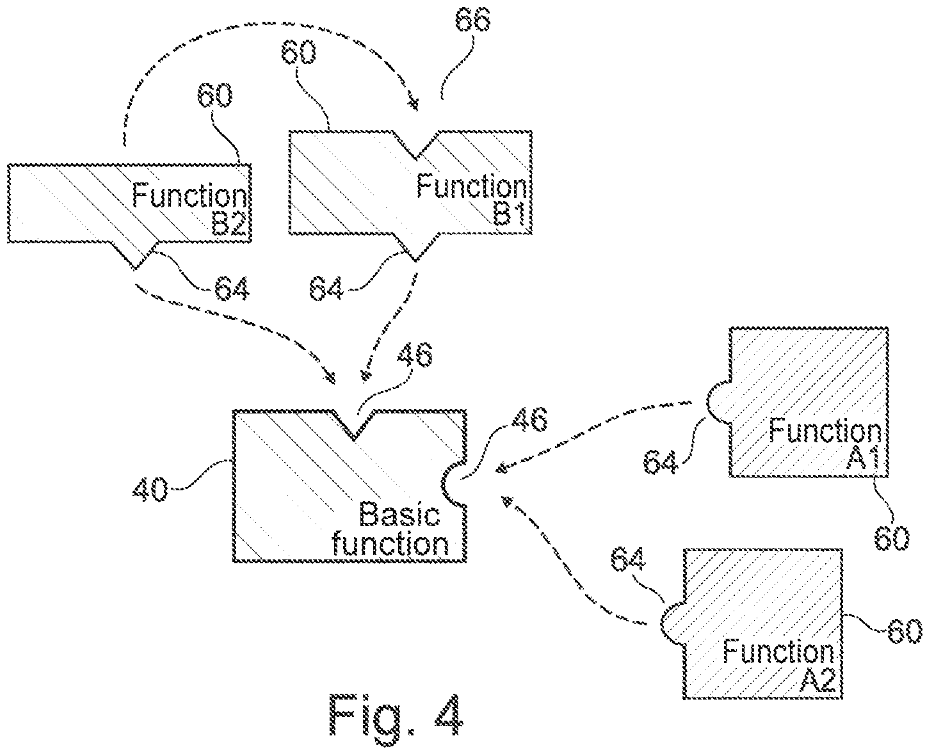
Figure 5:
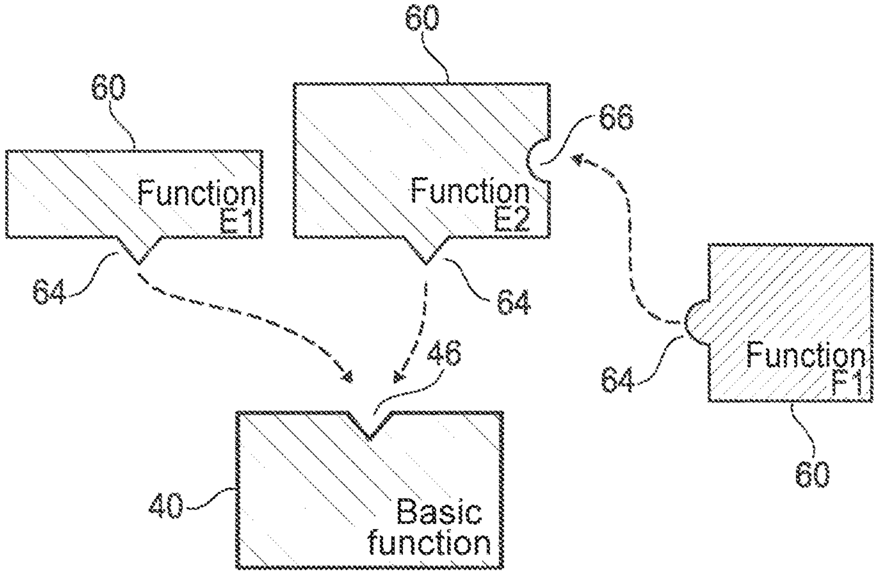
Figure 6:
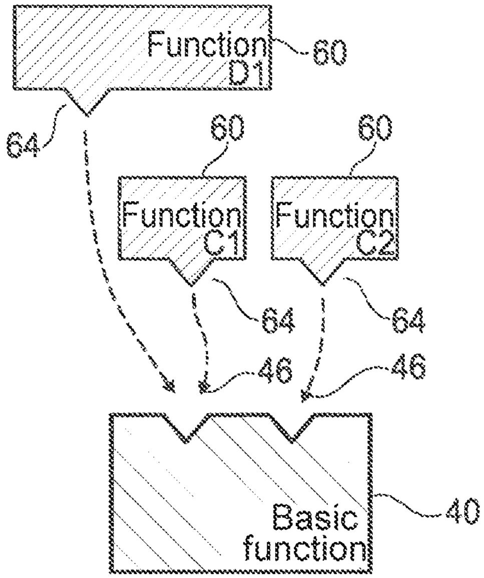
Figure 7:
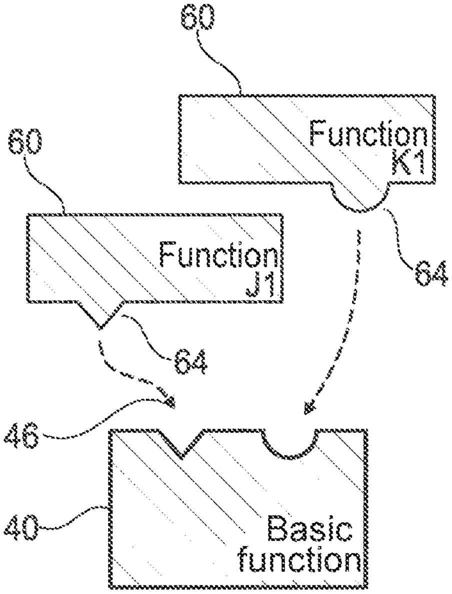
Figure 8:
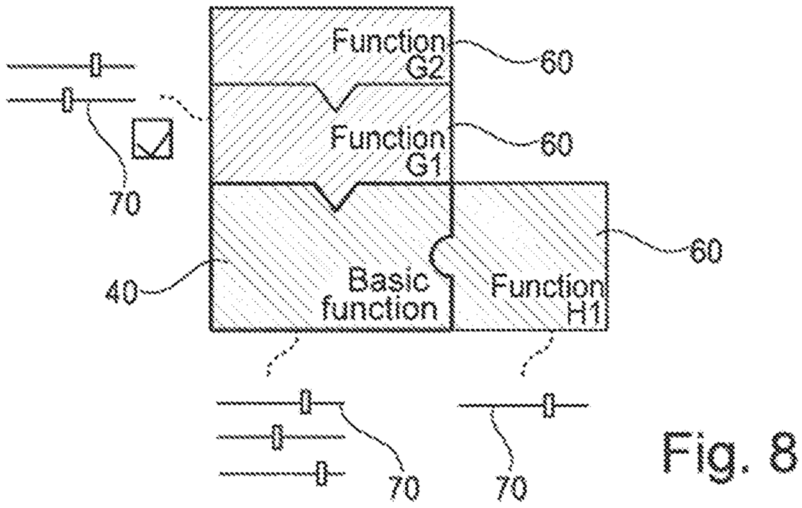
Figure 9:
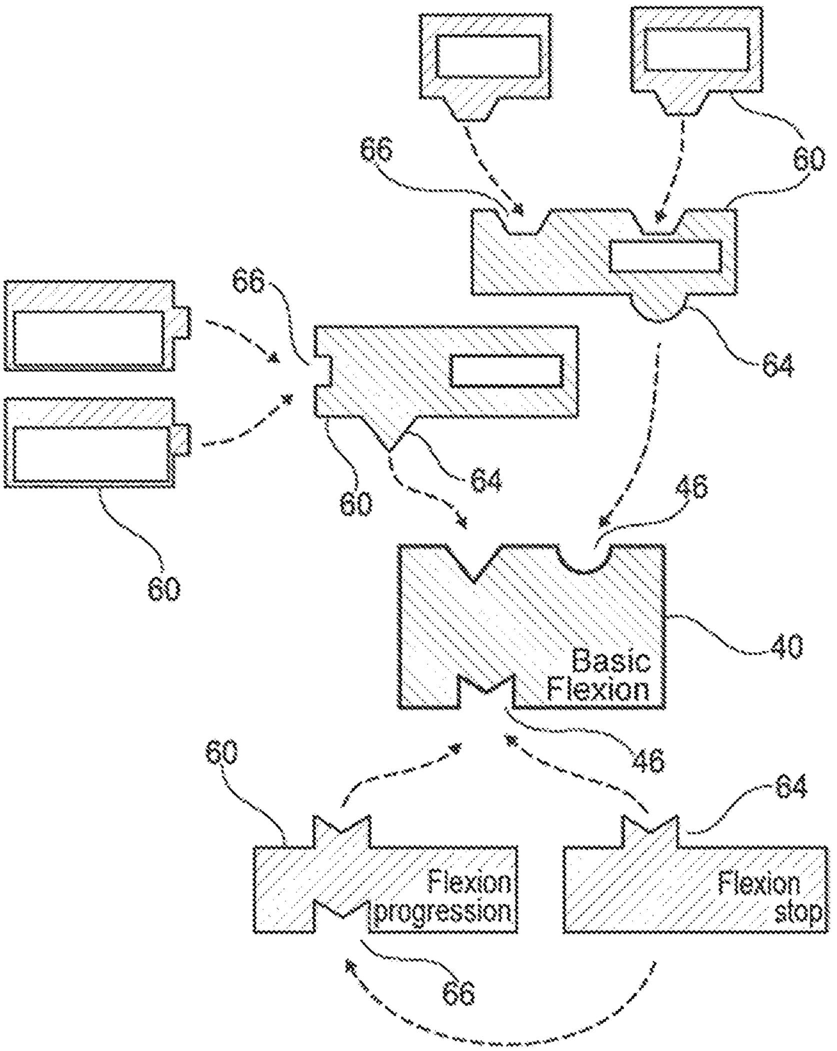
Figure 10:
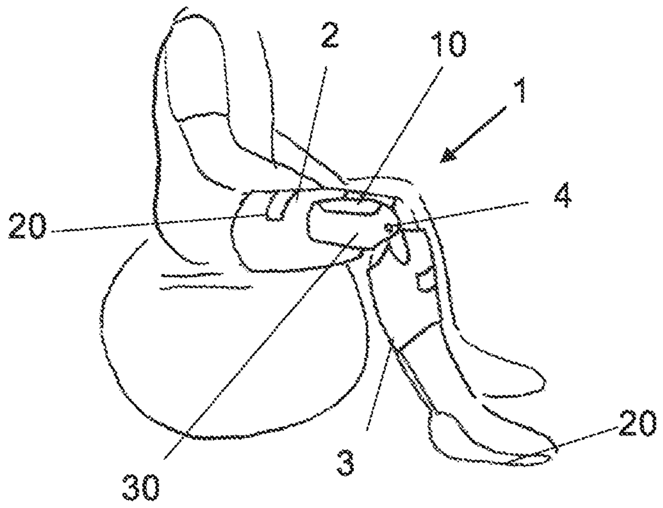
Figure 11:
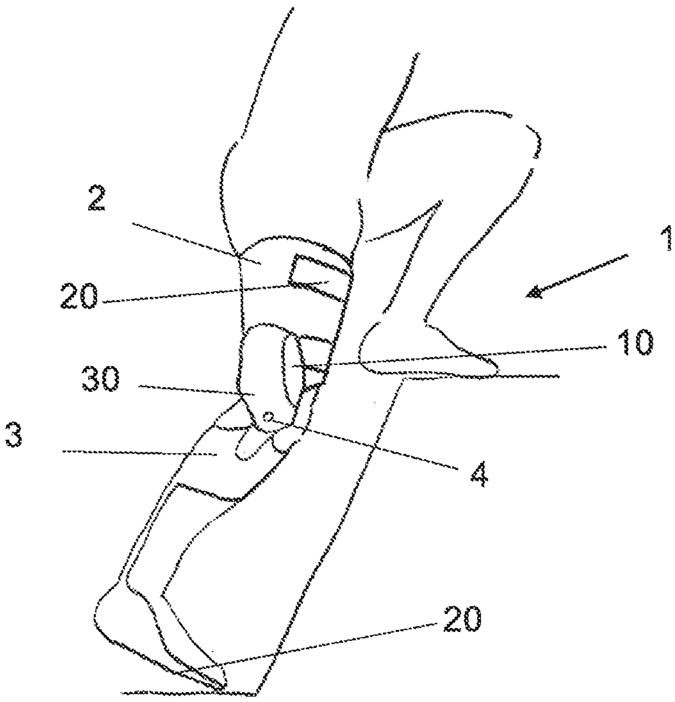
Figure 12:
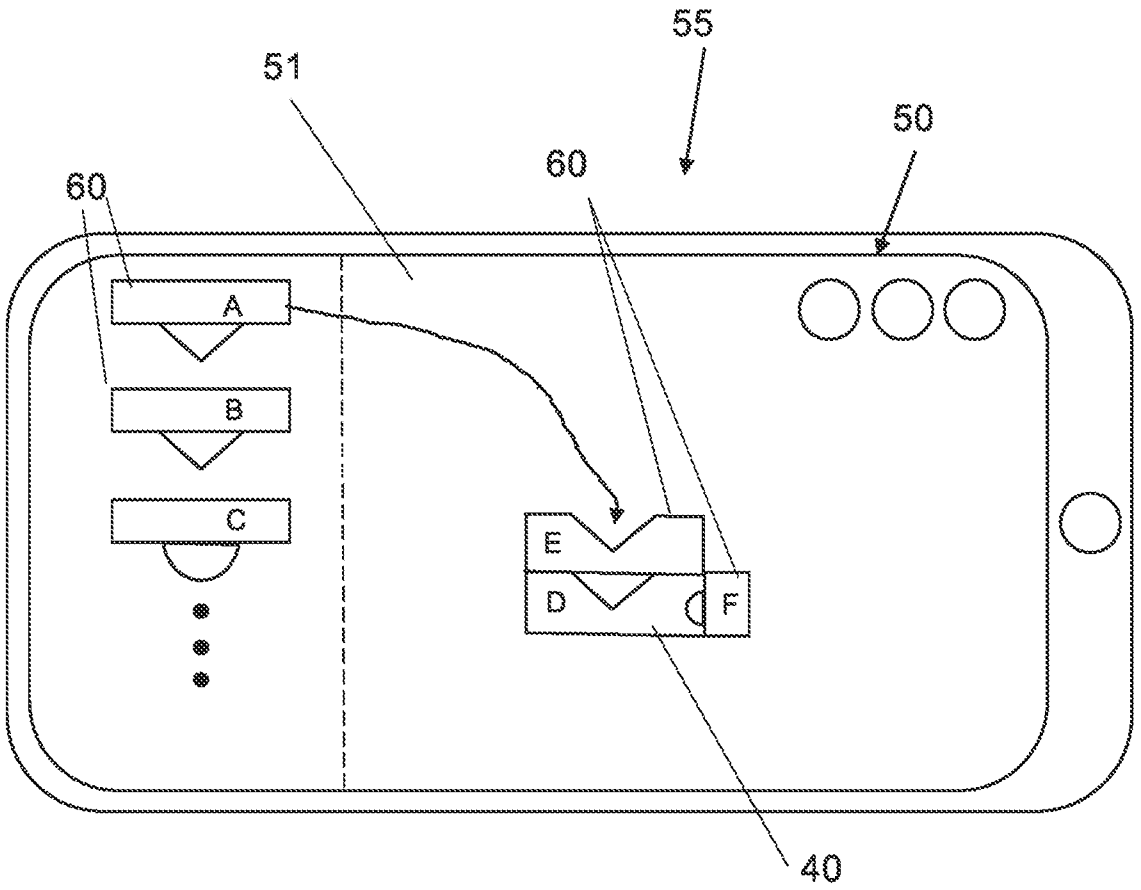
Figure 13:
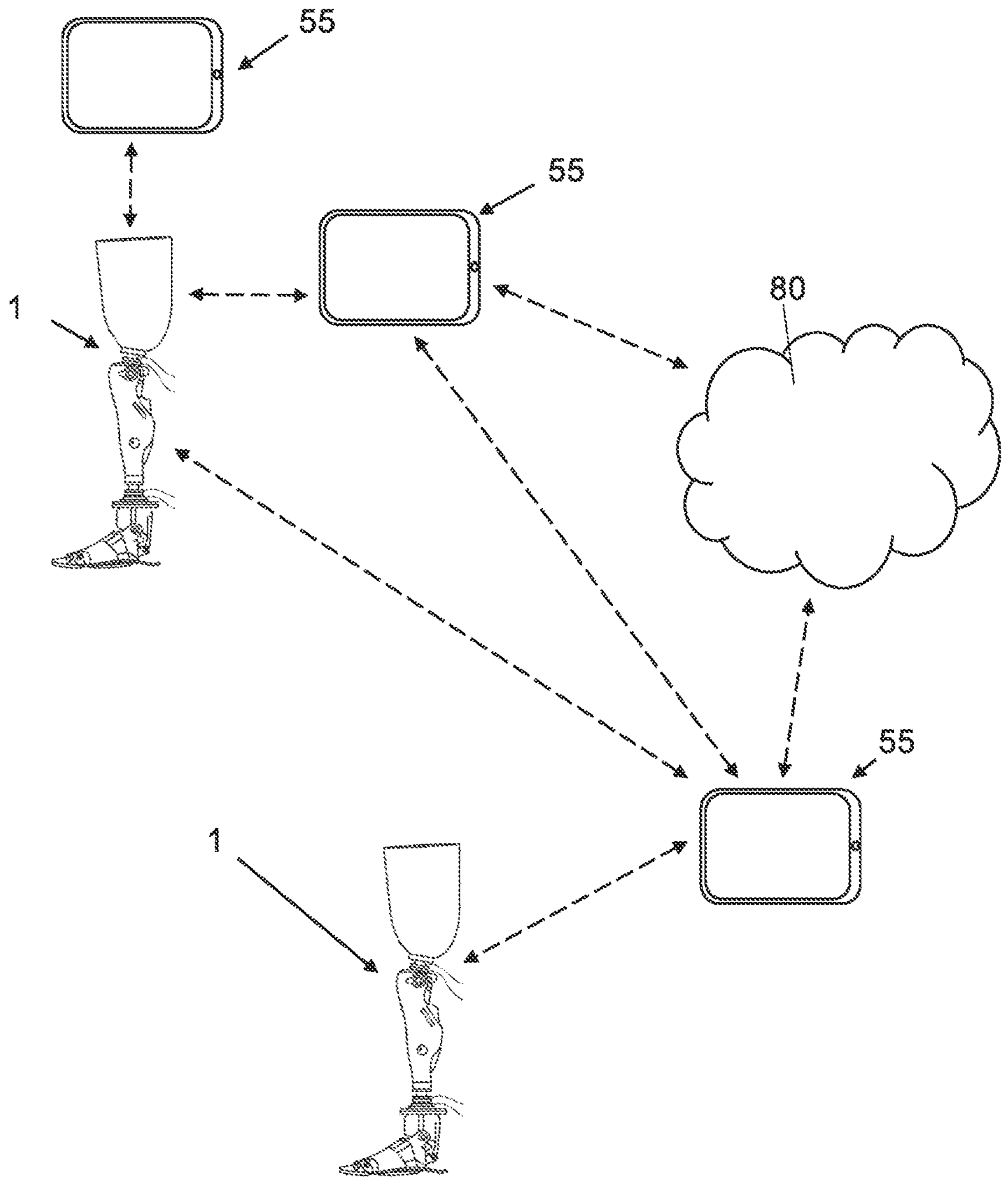

Exemplary embodiments of the invention will be discussed in more detail below on the basis of the appended figures. In the figures:

FIG. 1—shows a schematic representation of a prosthesis of an upper extremity as an orthopedic device;

FIG. 2—shows a schematic representation of a prosthesis of a lower extremity as an orthopedic device;

FIG. 3—shows a schematic representation of the modular principle;

FIG. 4—shows a variant with expansion options;

FIG. 5—shows a variant with additional interfaces;

FIG. 6—shows a variant with mutually exclusive add-on function blocks;

FIG. 7—shows a variant of FIG. 6;

FIG. 8—shows a variant with adjustable parameters;

FIG. 9—shows a further exemplary embodiment;

FIG. 10—shows an orthopedic device in the form of an orthosis;

FIG. 11—shows an orthosis according to FIG. 10 when walking;

FIG. 12—shows a detailed view of an external apparatus with an interface device; and FIG. 13—shows a schematic representation of a network of a plurality of orthopedic devices.

FIG. 1 shows a schematic representation of an orthopedic device 1 in the form of a prosthesis of an upper extremity. The orthopedic device 1 has a prosthesis socket for contact with a forearm. A plurality of sensors 20 in the form of surface electrode pairs are arranged inside the prosthesis socket. These sensors 20 are coupled to a data processing device 10, which is likewise arranged inside the forearm socket. The necessary software and hardware components are present in the data processing device 10, in particular processors, memories, energy stores are communication interfaces, filters and optional amplifiers for processing the sensor data and, from these, transmitting control signals to an actuator 30. In the exemplary embodiment shown, a multiplicity of actuators 30 are fastened in the prosthetic hand and in the coupling of the prosthetic hand to the forearm socket. In the exemplary embodiment shown, the actuators are in the form of electric motors, which enable a displacement of the prosthetic hand, for example, about an axis of rotation in the longitudinal extension of the forearm socket and a displacement of the prosthetic fingers relative to a base body of the prosthetic hand. The exemplary embodiment makes it clear that a multiplicity of functions can be implemented within the prosthetic hand. Different types of grips, different movement modes, different adjustment speeds, and gripping forces can be set and customized in situation-dependent fashion and on the basis of the respective user. For improved clarity, a memory 15 is shown as an external component; such a memory 15 can naturally also be embodied as part of the data processing device 10.

Furthermore, there is a wireless interface to an interface device 50, via which data can be exchanged wirelessly. The interface device 50 can be in the form of a cellular phone, portable computer, tablet, or other data processing device with a user interface. The interface device has a user interface 51, which can be in the form of a touch-sensitive surface, for example. Alternatively, the user interface can be in the form of a keyboard equipped with alphanumeric characters or function keys. The user interface 51 as a keyboard can also be generated electronically. In the exemplary embodiment shown, the interface device 50 is embodied as an external apparatus 55; in principle, it is also possible for the interface device 50 to be designed integrated into the orthopedic device 1, for example as a part of the surface of a prosthetic socket. It is possible to display user interface objects 52 on the user interface 51, the function of user interface objects will be explained in more detail below.

A variant of an orthopedic device in the form of a prosthetic knee joint with an upper part and a lower part pivotably mounted thereon is shown in FIG. 2. A prosthetic foot is fastened to the distal end and a thigh socket or thigh tube is fastened to the proximal end. The prosthetic knee joint 1 likewise has a control device 10 with a memory 15, sensors 20, for example acceleration sensors, position sensors, IMU, force sensors, temperature sensors, and more similar types of sensors 20, are connected to the data processing device 10. The interface device 50 with the user interface 51 is shown on the outside of the housing of the orthopedic device. Adjustment devices such as sliders or graphic adjustment symbols are shown below the interface device 50 and enable parameters to be changed by way of a mechanical adjustment or touch-sensitive surfaces. An actuator 30 in the form of a resistance device is arranged around a pivot axis about which the upper part of the prosthetic knee joint can be pivoted relative to the lower part, and said actuator renders it possible to adjust the flexion resistance and/or extension resistance on the basis of the processed sensor signals. Alternative actuators 30 can be present, for example adjustment devices for dampers, magnetic fields for magnetorheological resistance devices, drives that can be switched as resistance devices, active drives, energy stores, switchable energy stores, and the like.

To control the respective orthopedic device, sensor data is recorded by the sensors 20 or electrodes, processed in the data processing device 10, and transmitted to the respective actuator 30. A basic functionality is configured as basic equipment in the data processing device 10, via which the functions of the respective actuator 30 are defined. With this basic setting or basic functionality, it is possible to operate the respective orthopedic device safely. In order to adapt to the respective user, it is desirable and often necessary to implement further functionalities that go beyond the basic functionality. According to the invention, these add-on functionalities are stored in what are known as add-on function blocks, which are provided for the user in the respective interface device 50. The user can either be the orthopedic technician or the person who adapts the orthopedic device to the respective user; in principle, there is also the possibility that the user of the respective prosthesis, orthosis or exoskeleton or another orthopedic device carries out the adaptation. Functionalities which are not present in the basic function block or are present in a different configuration or in a different combination are stored in the add-on function blocks or in the at least one add-on function block. Since not all add-on functionalities are fully compatible with the basic functionality, the invention provides for a check of the overall functionality to be carried out when an add-on function block is added to the basic function block. An overall functionality for the orthopedic device 1 is generated as part of the determined compatibility of the combination of the function blocks, that is to say the basic function block and the add-on function block(s). If the functionalities of the basic function block and the add-on function block initially are not fully compatible, at least one functionality is adapted so that an overall functionality for the orthopedic device can be achieved following the addition of the add-on function block. In this case, the add-on functionality, the basic functionality or both functionalities can be adapted so that overall there is a safe overall functionality. In principle, there is also the possibility that instead of the functional scope of one or more add-on functionalities or the basic functionality being adapted, the integration of the selected add-on functionality is rejected because, for example, it is not compatible with other functionalities that have a higher priority and would compromise the safety or functionality of the overall system.

FIG. 3 shows a schematic representation of this modular principle. A basic functionality 40 has two interfaces 46, which are represented graphically differently. An add-on function block 60 likewise has an interface 64 which, in the exemplary embodiment shown, is only compatible with one of the two interfaces 46 of the basic function block 40. As indicated by the brackets, the two function blocks 40, 60 are connected to one another. As a result, the two function blocks 40, 60 can influence each other, as shown in the upper right illustration of FIG. 3. Alternatively, it is possible that there is only one-sided influencing of one function block on the other, in the exemplary embodiment shown from the add-on function block 60 on the basic function block 40. The overall functionality then results dependent on the coordination of the functionalities between the function blocks 40, 60.

A variant of the invention is shown in FIG. 4, in which a basic function block 40 has two different interfaces 46, like in FIG. 3. A total of four further add-on function blocks 60 which are couplable to the basic function block 40 are provided. A first add-on function block 60 without further combination options or a second add-on function block 60 with a further interface 66 can be coupled to the upper side of the basic function block 40. The respective interface 64, which is compatible with the respective interface 46 on the basic function block 40, is also usable for decoupling the first add-on function block 60 in the example shown. This results in an extension by two add-on function blocks 60 on the upper side and the first interface 46 of the basic function block. The second interface 46 is couplable to a different add-on function block 60, these add-on function blocks 60 have no further interfaces for the purpose being coupled to one another, with the result that only a single add-on function block is present at this interface 46. In the exemplary embodiment shown, there consequently is one add-on function block 60 which has two interfaces 64, 46, while the other add-on function blocks 60 only have one interface 46.

A variant of the invention is shown in FIG. 5, in which a basic function block 40 has only one interface 46. It can be occupied by two add-on function blocks 60, with one add-on function block 60 having another interface 66 which can be coupled to an interface 64 of another add-on function block 60. Hence, for the structure of an overall functionality, there is a choice between three combinations of the basic function block 40: either with a first add-on function block 60 without an expansion option, or with a second add-on function block 60 with an expanded option, without the latter being perceived, and finally there is the combination of the basic function block 40 with the add-on function block 60 that has been extended by an add-on function block 60.

FIG. 6 shows a variant in which a plurality of interfaces 46, to which a number of add-on function blocks 60 can be coupled, are provided on a basic function block 40.

It is possible here that one add-on function block 60 prevents the coupling of further add-on function blocks, that is to say a coupling of further add-on function blocks is no longer possible with said add-on function block. In the case of another functionality of an add-on function block 60, it is possible for a plurality of add-on function blocks to be arranged next to one another as alternatives or in combination with one another at the interfaces 46 and be able to be combined with the latter.

FIG. 7 shows a variant of these blocking interface configurations. Arranged or formed on the basic function block 40 there are two different interfaces 46, to which only one add-on function block 60 with the corresponding fitting interface 64 can be coupled in each case.

A development of the invention is shown in FIG. 8, in which the basic function block 40 is coupled to a total of three add-on function blocks 60. The respective functionalities are checked for compatibility and an overall functionality is generated. In order to adapt to the different needs of a user, it is possible to set appropriate parameters of the respective functionality by way of regulators 70 or adjustment devices. This parameterization is also checked for compatibility with the settings of the other functionalities. This rules out an erroneous adaptation of a functionality resulting in an unwanted interaction with another functionality, which interaction would endanger the safe use of the orthopedic device 1. The parameter range over which parameters can be adjusted can also be stored in the basic functionality of the basic function block 40. An adjustment beyond this parameter range or beyond this value range can be interrupted or prevented. Feedback can also be given via a warning signal that such a combination of basic functionality and add-on functionalities is not possible in a specific parameter range. Corresponding positive feedback can be given if an adjustment is accepted.

FIG. 9 shows an exemplary embodiment of the modular structure of basic functionalities and add-on functionalities. A basic function block 40 with three different interfaces 46 is shown. If a control of a prosthetic knee joint is stored as the basic functionality, a flexion stop, for example, can be set or adjusted by the addition of an add-on function block 60. An integration of such an add-on function block would prevent adjustability or settability with regard to the position of the flexion stop. There is therefore also the option of adding a flexion progression to the basic functionality by way of an alternative add-on function block, to which a flexion stop can be coupled since such an add-on function block 60 has an additional interface 66 for coupling and combining with the flexion stop module.

Furthermore, other control blocks or functional elements can be coupled to one of the two remaining interfaces 46. The one add-on function block has only one additional interface 66, to which only one further module can be coupled as an extension or a restriction or for the modification of the add-on function. If a different add-on function block 60 with two additional interfaces 66 is coupled instead of the first add-on function block with only one additional interface, then two further add-on function blocks 60 are couplable as alternatives or in combination.

If there are a plurality of modes, for example walking or cycling in the case of orthopedic devices for the lower extremities or different types of grips in the case of prosthetic hands, then each mode can be composed of a basic function and add-on function. However, it is also possible that not every mode is freely programmable, but only individual modes. Switching between the modes takes place, for example, via biosignals such as co-contractions, contraction patterns, movement patterns, via an interface that can be controlled via an app, for example, or in any other, optionally also freely programmed, way.

FIGS. 10 and 11 show an orthopedic device 1 in the form of an orthosis. The user of the orthopedic device 1 is seated in FIG. 10, and shown while overcoming an obstacle in FIG. 11. The orthosis has an upper part 2 and a lower part 3 which are connected to one another in an articulated manner about a pivot axis 4. The upper part 2 is designed as a thigh cuff, the lower part 3 as a receiving shell for the lower leg and the foot. The orthopedic device 1 is fastened to the thigh and the lower leg of the user of the orthosis by way of suitable fastening elements, for example belts, straps, hook-and-loop fasteners, buckles or snap fasteners. Sensors 20 which are only shown schematically are arranged both on the upper part 2 and the lower part 3.

The sensors 20 can be in the form of, for example, position sensors, pressure sensors, acceleration sensors or other sensors for the purpose of recording load data, speed data, and other physical variables. It is likewise possible that the sensors 20 record temperatures. The sensors 20 are coupled either by cable or wirelessly to a data processing device 10 which is fastened or formed on the upper part 2 in the exemplary embodiment shown. The data processing device 10 processes the sensor data and is equipped with the necessary software components and hardware components. The data processing device 10 is coupled to a schematically shown actuator 30, by means of which it is possible to make adjustments to resistance devices such as dampers, magnetorheological brakes or the like or to displace the upper part 2 relative to the lower part 3. For this purpose, the actuator 30 is then designed as a drive or motor. It is likewise possible for the actuator 30 to be in the form of a switchable energy store, for example a spring that can be tensioned and released. As described above in the explanations relating to FIGS. 1 and 2, different functional modes or movement modes can also be set depending on the situation in an orthopedic device 1 in the form of an orthosis for the lower extremity. This can be done either autonomously by the orthosis user or automatically on the basis of the sensor data. By way of example, if a position sensor 20 on the upper part 2 detects a substantially horizontal orientation of the upper part 2 with simultaneous relief of the lower part 3 and the absence of a relative movement about the pivot axis 4, a seat mode can be switched on automatically, the latter activating or deactivating the actuator 30 accordingly so that an undamped or almost undamped free mobility about the pivot axis 4 is made possible. On the other hand, if a stretched position with a loaded forefoot is recognized, like in FIG. 11, it is possible to deduce that an obstacle is being climbed over, with the result that accordingly different resistances against an extension or flexion, or else an assistance force by the actuator 30, are provided. The structure and design with basic function blocks and add-on function blocks, as described with reference to FIGS. 1 and 2 using the example of prostheses, is applied accordingly to the embodiment as an orthosis. Add-on function blocks can also be coupled to corresponding interfaces in the case of orthoses.

These add-on function blocks can exclude or enable further coupling of add-on function blocks to themselves. A plurality of interfaces can be provided on a basic function block and can be alternatively or additionally connected to add-on function blocks.

FIG. 12 shows a detailed representation of an external apparatus 55 in the form of a cellular phone or a tablet. The external apparatus 55 has an interface device 50 which is in the form of a graphical user interface. A touch-sensitive display is formed on the external apparatus 55 and, in addition to optical information transfer to a user, enables input via a touch-sensitive screen. A loudspeaker device (not shown) and a microphone are likewise present on the external apparatus 55 for the purpose of recording acoustic signals or carrying out a corresponding combination of different functionalities via voice control.

Various add-on function blocks 60 that are combinable with a basic function block 40 are shown on the display 51. The basic function block 40 is shown in a central position on the display 51, available add-on function blocks 60 are arranged next to it and one below the other in a separate area of the display 51. The function blocks 60 shown in the separate area can be adapted dynamically in this case, for example so as to only display function blocks that can be added to the configuration. In the exemplary embodiment shown, three add-on function blocks 60 provided with different functionalities are arranged one below the other and are identified by the letters A to C. The dots underneath indicate that further add-on function blocks 60 can be moved into the display 51 by scrolling, for example, in order to then be selected. An add-on function block A can be connected and added to the interface of another add-on function block 60, specifically the add-on function block E, by dragging and dropping as indicated by the arrow. Alternatively, it is possible by selecting one of the interfaces, for example the upper interface of the function block E by touching the display, to have a selection of function blocks which can be added to this interface displayed in the separate area. The corresponding function block is added by drag-and-drop or a simple selection. Two add-on function blocks 60 are already arranged on the basic function block 40. Likewise, already existing add-on function blocks 60 can be removed again, and so a new overall configuration with a new overall functionality can be generated. Additional menu items, which are indicated by the circles in the upper right corner of the display 51, can be used to save configurations that have been created, to transfer these configurations to the cloud or to the orthopedic device, to share these configurations with third parties or to load these configurations.

FIG. 13 shows a schematic representation of a network of a plurality of orthopedic devices 1, which are connected to one another and to an external IT infrastructure 80. The IT infrastructure 80 is advantageously in the form of what is known as a cloud and is a computer network which makes available storage space, computing power and/or user software. An external apparatus 55, for example a tablet, a cellular phone, a laptop or another appropriate data processing device, is bidirectionally connected to a first orthopedic device 1, to a prosthesis in the exemplary embodiment shown. The first external apparatus 55 can be, for example, a smartphone of the user of the orthopedic device. In addition, the first orthopedic device 1 can be data-connected to another mobile terminal, a tablet or a computer, for example via a wireless interface, a radio link or a similar data transmission device. From there, the data is transmitted to the so-called cloud 80 and, optionally, processed and transmitted back again. Provision is likewise made for the add-on function blocks or settings of the first orthopedic device 1 to be evaluated, transmitted to third parties, and/or stored. The data can be transmitted from the cloud 80 to a further external apparatus 55 which is coupled to a second orthopedic device 1. As an alternative or in addition to the intermediate step, in which the data is transmitted via the cloud 80 from the first orthopedic device 1 to the second orthopedic device 1, the data can also be transmitted directly via the second external apparatus 55 or directly via the third external apparatus 55 to the first external apparatus 55 and back.

The compatibility of the function blocks can be checked in one of the other external apparatuses 55 or in the cloud 80, with the result that computing capacity in the orthopedic device 1 does not have to be used to this end. Likewise, predefined programs or templates can be transmitted from the other external apparatuses 55 and/or the cloud 80 to the respective orthopedic device 1 or to a directly assigned external apparatus 55 or an interface device arranged directly on the orthopedic device 1. The orthopedic devices are networked and there is data exchange and data evaluation.

The invention claimed is:

1. A method for configuring a control for an orthopedic device having at least one data processing device, sensors coupled thereto, and an actuator which is activated or deactivated by the data processing device, the control having a basic function block in which a basic functionality of the actuator is defined, the method comprising:

making a plurality of add-on function blocks which have different add-on functionalities available to an interface device from a memory;

receiving a selection of at least one add-on function block via the interface device;

adding the selected at least one add-on function block to the basic function block, wherein an interface is present between the basic function block and the at least one add-on function block, and further comprising checking a compatibility of the functionalities and generating an overall functionality, with, in the case of a lack of compatibility at the outset, at least one functionality being adapted to produce the compatibility or integration of the add-on functionality being rejected.

2. The method of claim 1, further comprising successively adding a plurality of add-on function blocks to the basic function block, and checking the compatibility with the currently existing overall functionality for each new add-on function block.

3. The method of claim 1, wherein at least one parameter of at least one of the basic functionality or add-on functionality is adjustable via the interface device.

4. The method of claim 1, wherein each add-on functionality is assigned a prioritization value and the compatibility and adaptation of the respective functionality is checked using the prioritization values.

5. The method of claim 1, further comprising providing a graphical user interface as the interface device, the add-on functionalities being displayed on said graphical user interface as user interface objects.

6. The method of claim 5, wherein the compatibility of different add-on function blocks with one another or with the current combination of basic function block and at least one add-on function block is displayed graphically.

7. The method of claim 5, wherein at least one of a color or graphic combinability of an add-on function block with at least one of the basic function block or another add-on function block is displayed on the user interface objects.

8. The method of claim 1, wherein the said method is implemented on the data processing device.

9. The method of claim 1, wherein an interface for at least one further add-on function block is formed on an add-on function block.

10. The method of claim 1, wherein at least one of the basic function block or an add-on function block has a plurality of interfaces, at least one of which is blocked as a result of another interface being occupied with an add-on function block.

11. The method of claim 1, wherein at least one of the compatibility of the function blocks or the integration of a plurality of function blocks into an overall functionality is checked in an external apparatus.

12. The method of claim 1, wherein predefined programs or templates are used to create a function block.

13. The method of claim 1, wherein the data processing device transmits data to external devices or receives data from external devices via a communication interface.

14. An orthopedic device comprising a data processing device which is configured and designed to carry out the method of claim 1, and comprising a user interface with input means for receiving user inputs.

15. A non-transitory computer-readable medium storing program code which, when loaded into a data processing device, brings about execution of the method as claimed in claim 1.

* * * * *